United States Patent [19]

Kolassa et al.

[11] Patent Number: 4,994,106

[45] Date of Patent: Feb. 19, 1991

[54] CYCLOHEXENONE COMPOUNDS, THEIR PREPARATION AND THEIR USE FOR CONTROLLING UNDESIRABLE PLANT GROWTH

[75] Inventors: Dieter Kolassa, Ludwigshafen; Juergen Kast, Boehl-Iggelheim; Michael Keil, Freinsheim; Ulrich Schirmer, Heidelberg; Norbert Meyer, Ladenburg; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 321,063

[22] Filed: Mar. 9, 1989

[51] Int. Cl.$^5$ .............................................. A01N 33/24
[52] U.S. Cl. ...................................... 71/121; 564/256
[58] Field of Search ........................... 564/256; 71/121

[56] References Cited

U.S. PATENT DOCUMENTS

| | | | |
|---|---|---|---|
| 3,950,420 | 4/1976 | Sawaki et al. | 564/256 |
| 3,989,737 | 11/1976 | Sawaki et al. | 564/256 |
| 4,011,256 | 3/1977 | Sawaki et al. | 564/256 |
| 4,075,239 | 2/1978 | Sawaki et al. | 71/98 |
| 4,482,740 | 11/1984 | Ewataki et al. | 564/99 |
| 4,504,305 | 3/1985 | Iwataki et al. | 71/98 |
| 4,666,510 | 5/1987 | Watson et al. | 564/256 |
| 4,692,553 | 9/1987 | Keil et al. | 564/185 |

OTHER PUBLICATIONS

Tetrahedron Letters, No. 29, pp. 2491-2492, Pergamon Press (1975).

Abstract of Japanese Preliminary Published Application No. 79/073052

Primary Examiner—James H. Reamer
Attorney, Agent, or Firm—Keil & Weinkauf

[57] ABSTRACT

Cyclohexenone compounds of the formula I

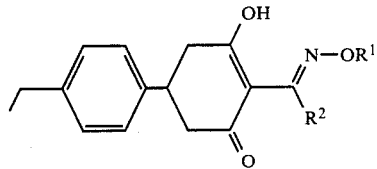

where the substituents have the following meanings:
$R^1$ is $C_3$–$C_4$-alkenyl, $C_3$–$C_4$-alkynyl, $C_2$–$C_4$-haloalkyl, $C_2$–$C_4$-haloalkenyl, $C_2$–$C_4$-alkoxyalkyl or a radical $CH_2$—$R^3$, where
  $R^3$ is a 5 ring heterocycle with one to three nitrogen atoms and/or one to two oxygen atoms and/or one sulfur atom as hetero-atoms, which may bear up to two double bonds and one or two of the following substituents: $C_1$–$C_4$-alkyl, $C_1$–$C_4$-alkoxy, $C_1$–$C_4$-alkylthio, halogen, trifluoromethyl, $C_1$–$C_4$-alkoxymethyl, $C_1$–$C_4$-alkylthiomethyl and/or vinyl, or phenyl which may bear one to three of the following groups: $C_1$–$C_4$-alkyl, $C_1$–$C_4$-alkoxy, $C_1$–$C_4$-alkylthio, halogen, trifluoromethyl, nitro and/or $C_1$–$C_4$-dialkylamino, and
$R^2$ is $C_1$–$C_4$-alkyl, and their agriculturally acceptable salts, processes for their manufacture, and their use.

9 Claims, No Drawings

CYCLOHEXENONE COMPOUNDS, THEIR PREPARATION AND THEIR USE FOR CONTROLLING UNDESIRABLE PLANT GROWTH

The present invention relates to cyclohexenone compounds of the formula I

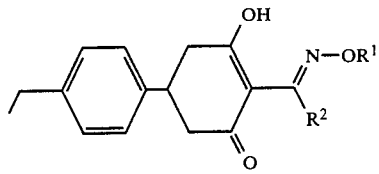

where $R^1$ is $C_3$- or $C_4$-alkenyl, $C_3$- or $C_4$-alkynyl, $C_2$-$C_4$-haloalkyl, $C_2$-$C_4$haloalkenyl, $C_2$-$C_4$-alkoxyalkyl or $CH_2$—$R^3$, $R^3$ is a 5-membered heterocyclic ring which has 1 to 3 nitrogen atoms and/or 1 or 2 oxygen atoms and/or a sulfur atom as heteroatoms and not more than 2 double bonds and may carry one or two of the substituents $C_1$-$C_4$-alkyl, $C_1$-$C_4$-alkoxy, $C_1$-$C_4$-alkylthio, halogen, trifluoromethyl, $C_1$-$C_4$-alkoxymethyl, $C_1$-$C_4$-alkylthiomethyl and/or vinyl or a phenyl radical which may carry one to three of the groups $C_1$-$C_4$-alkyl, $C_1$-$C_4$-alkoxy, $C_1$-$C_4$-alkylthio, halogen, trifluoromethyl, nitro and/or $C_1$-$C_4$-dialkylamino, and $R^2$ is $C_1$-$C_4$-alkyl, and their agriculturally acceptable salts.

The present invention furthermore relates to a process for the preparation of these compounds and methods for controlling undesirable plant growth using agents which contain the compounds I.

The compounds I may occur in a plurality of tautomeric and stereoisomeric (E and Z isomerism) forms, all of which are embraced by the claim.

The literature describes 3-hydroxy-2-cyclohexen1-ones which carry a substituted phenyl radical in the 5-position and are suitable for controlling undesirable grasses in broad-leaved crops (DE-A 24 39 104). Phenylsubstituted cyclohexenone compounds, which are used for controlling grass weeds in crops such as corn, wheat, barley and rice are also disclosed (DE-A 32 48 554, DE-A 33 29 017 and DE-A 30 47 924).

It is an object of the present invention to provide compounds which have high selectivity at a low application rate, ie. control undesirable plants without damaging the crops.

We have found that this object is achieved by the cyclohexenone compounds defined at the outset.

The cyclohexenones of the formula I can be obtained in a known manner from known raw materials; for example, the corresponding cyclohexenone of the formula II

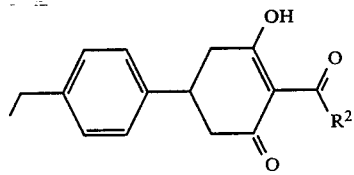

can be reacted with a hydroxylamine $R^1ONH_2$.

Advantageously, the reaction is carried out in the heterogeneous phase in a solvent at not more than 80° C. in the presence of a base, and the hydroxylamine source used is the ammonium compound of the said hydroxylamine.

Examples of suitable bases are carbonates, bicarbonates, acetates, alcoholates or oxides of alkali metals or alkaline earth metals, in particular sodium hydroxide, potassium hydroxide, magnesium oxide or calcium oxide. Organic bases, such as pyridine or tertiary amines, can also be used. The base is added, for example, in an amount of from 0.5 to 2 moles, based on the ammonium compound (DE-A-34 33 767).

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as dioxane and tetrahydrofuran.

The reaction is complete after a few hours, and the end product can be isolated by evaporating down the mixture, distributing the residue in methylene chloride/water and distilling off the solvent under reduced pressure.

It is also possible to use the free hydroxylamine base directly, for example in the form of an aqueous solution; depending on the solvent used for the other reactant, a one-phase or two-phase reaction mixture is obtained.

Examples of suitable solvents for this reaction are alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as tetrahydrofuran.

Alkali metal salts of the compounds I can be obtained by treating the 3-hydroxy compounds with sodium hydroxide, potassium hydroxide, a sodium alcoholate or a potassium alcoholate in aqueous solution or in an organic solvent, such as methanol, ethanol, acetone or toluene.

Other metal salts, for example the manganese, copper, zinc, iron, calcium, magnesium and barium salts, can be prepared from sodium salts in a conventional manner, as can ammonium, phosphonium, sulfonium and sulfoxonium salts by using ammonia or phosphonium, sulfonium or sulfoxonium hydroxides.

The compounds of type II can be prepared, for example, from the corresponding cyclohexane-1,3-diones of the formula III

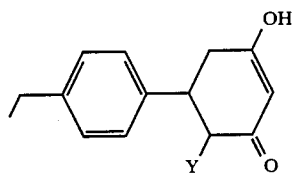

where y is hydrogen or methoxycarbonyl, by known methods [Tetrahedron Lett. (1975), 2491].

It is also possible to prepare the compounds of the formula II via the enolester intermediates, which are obtained in the reaction of compounds of the formula III with acyl chlorides in the presence of a base and are then subjected to a rearrangement reaction with certain imidazole or pyridine derivatives (Japanese Preliminary Published Application 79/063052).

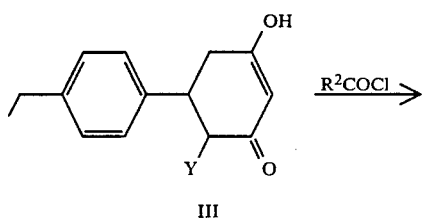

III

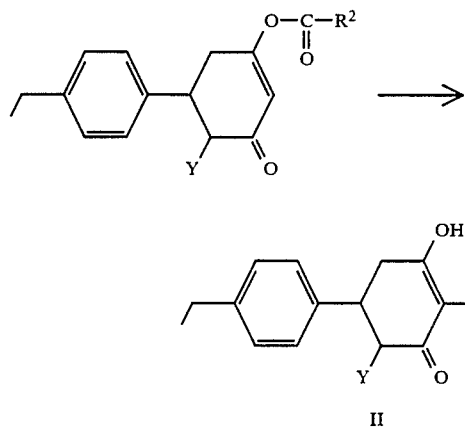

II

Compounds of the formula I are obtained using known, commercial compounds are starting materials and by a number of known process steps, as shown in the scheme below and illustrated by a practical example.

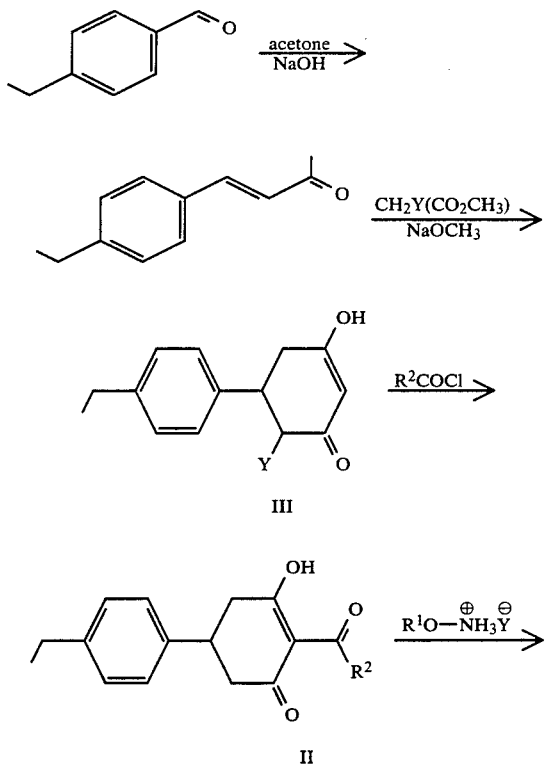

II

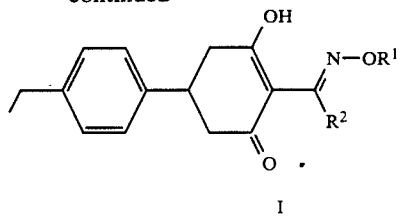

I

Because of the biological activity, preferred cyclohexenone compounds I are those in which the radicals have the following meanings:

$R^1$ is alkenyl, such as allyl, buten-2-yl, buten-3-yl and 2-methylbuten-2-yl, in particular allyl and buten-2-yl, alkynyl, such as prop-2-ynyl, but-2-ynyl, but-3-ynyl and 1-methylprop-2-ynyl, in particular prop-2-ynyl and but-2-ynyl; haloalkyl, such as 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, in particular 2-chloroethyl, 2-fluoroethyl, 2,2,2-trifluoroethyl and pentafluoroethyl; haloalkenyl, such as 2-chloroprop-2-enyl, 3-chloroprop-2-enyl or 3,3,2-trichloroprop-2-enyl, in particular 3-chloroprop-2-enyl; alkoxyalkyl, such as methoxymethyl, ethoxymethyl, methoxyethyl and ethoxyethyl, in particular methoxyethyl and ethoxyethyl; phenyl which may carry one to three of the following substituents: nitro, trifluoromethyl, halogen, such as fluorine, chlorine, bromine or iodine, in particular fluorine or chlorine, alkyl, such as methyl, ethyl, propyl, 1-methyl-ethyl, butyl, 1-methylpropyl, 2-methylpropyl oz 1,1-dimethylethyl, in particular methyl or ethyl, alkoxy, such as methoxy, ethoxy, propoxy, 1-methylethoxy, butoxy, 1-methylpropoxy, 2-methylpropoxy or 1,1-dimethylethoxy, in particular methoxy or 1-methylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio and/or dialkylamino, such as dimethylamino, ethylmethylamino or dimethylamino, in particular dimethylamino, or a radical —$CH_2$—$R^3$, where $R^3$ is tetrahydrofuranyl, tetrahydrothiophenyl, dioxolanyl, dithiolanyl, oxathiolanyl, dihydrofuranyl, dihydrothienyl, pyrrolinyl, pyrazolinyl, imidazolinyl, isoxazolinyl, oxazolinyl, isothiazolinyl, thiazolinyl, furanyl, thienyl, pyrrolyl, pyrazolyl, isoxazolyl, oxazolyl, isothiazolyl, thiazolyl, oxadiazolyl, thiadiazolyl, imidazolyl, oxadiazolyl, thiodiazolyl or triazolyl, in particular thiophenyl or isoxazolyl, and this heterocyclic structure may carry one or two of the following substituents: $C_1$–$C_4$-alkyl as stated above, in particular methyl, ethyl or isopropyl, $C_1$–$C_4$-alkoxy as stated above, in particular methoxy, ethoxy or isopropoxy, $C_1$–$C_4$-alkylthio as stated above, in particular methylthio or ethylthio, halogen as stated above, in particular fluorine or chlorine, alkoxymethyl, such as methoxymethyl, ethoxymethyl, propoxymethyl, isopropoxymethyl, butoxymethyl, 1-methylpropoxymethyl, 2-methylpropoxyethyl or 1,1-dimethylethoxymethyl, in particular methoxyethyl or ethoxymethyl, alkylthiomethyl, such as methylthiomethyl, ethylthiomethyl, propylthiomethyl, isopropylthiomethyl, butylthiomethyl, 1-methylpropylthiomethyl, 2-methylpropylthiomethyl or 1,1-dimethylethylethoxymethyl, thiomethyl in particular methylthiomethyl or ethylthiomethyl trifluoromethyl and/or vinyl and $R^2$ is $C_1-C_4$-alkyl, such as methyl, ethyl, propyl 1-methylethyl, butyl, 1-methylpropyl, 2-methylpropyl or 1,1-dimethylethel, in particular ethyl or propyl.

Suitable salts of the compounds of the formula I are agriculturally acceptable salts, for example alkali metal salts, in particular potassium salts or sodium salts, alkaline earth metal salts, in particular calcium salts, and also manganese salts, copper salts, zinc salts, iron salts and ammonium, tetraalkylammonium, benzyltrialkylammonium, trialkylsulfoxonium and trialkylsulfonium salts.

The cyclohexenones, or the herbicidal agents containing them, may be applied for instance in the form of directly sprayable solutions, powders, suspensions including high-percentage aqueous, oily or other suspensions dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol chloroform, carbon tetrachloride, cyclohexanol, cyclohexenone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol. alkylphenol polyglycol ethers, tributylphenyl polyglycol ethers, alkylaryl polyether alcohols, isotridecyl alcohol, fatty alcohol ethylene oxide condensates, ethoxylated castor oil polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

The cyclohexenone compounds may be formulated for instance as follows:

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 1 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 2 is dissolved in a mixture consisting of 40 parts by weight of cyclohexenone. 30 parts by weight of isobutanol. 20 parts by weight of the adduct of 7 moles cf ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 8 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 3 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformy distributing the mixture in 20,000 parts by weight of water, a spray liquor is obtained containing 0.1% by weight of the active ingredient.

VI. 3 parts by weight of compound no. 9 is intimately mixed with 97 parts by weight of particulate kaolin. A dust is obtained containing 3% by weight of the active ingredient.

VII. 30 parts by weight of compound no. 13 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 12 is intimately mixed with 2 parts of the calcium salt of dodecylbenzenesulfonic acid. 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched and the agents reach the soil or the unwanted plants growing beneath the crop plants (post-directed lay-by treatment).

The application rates depend on the objective to be achieved, the time of the year, the plants to be combated and their growth stage, and are from 0.01 to 3.0, preferably 0.05 to 1.0 kg of active ingredient per hectare.

In view of the number of application methods possible, the compounds according to the invention, or agents containing them, may be used in a further large number of crops for removing unwanted plants. The following crops are given by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rapeseed |
| *Brassica napus* var. napobrassica | swedes |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum*, *Gossypium herbaceum*, *Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | sorgo |
| *Spinacia oleracea* | spinach |
| *Theobroma cacao* | cacao plants |
| *Trifolium pratense* | red clover |
| *Triticum aestivum* | wheat |
| *Triticum durum* | durum wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the cyclohexenones of the formula I may be mixed and applied together with numerous representatives of other herbicidal or growth-regulating active ingredient groups. Examples of suitable components are diazines 4H-3,1 benzoxazine derivatives, benzothiadiazinones, 2,6-dinitroanilines, N-phenylcarbamates, thiolcarbamates halocarboxylic acids, triazines, amides, ureas, diphenyl ethers, triazinones, uracils, benzofuran derivatives, cyclohexane-1,3-dione derivatives, quinolinecarboxylic acids, phenyloxy- or heteroaryloxy-phenylpropionic acids and salts, esters and amides thereof, etc.

It may also be useful to apply the novel compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

MANUFACTURING EXAMPLES

The directions given in the synthesis examples below were employed, after appropriate modifications to the starting materials, to obtain further compounds of the formula I; the compounds obtained are listed in the tables below with physical data. Those compounds for which no data are given may be produced analogously from the appropriate materials. In view of their close structural similarity with the compounds produced and investigated, they are expected to have a similar action.

EXAMPLE 1

(a) 4(4-Ethylphenyl)-3-buten-2-one 20 ml of 10% strength sodium hydroxide solution is added to a mixture of 111.4 (0.83 mol) of 4-ethylbenzaldehyde, 133 g of acetone and 100 ml of water, and the mixture is stirred overnight at room temperature. It is then diluted with 300 ml of ice water and extracted five times, each time with 100 ml of dichloromethane. The extracts are dried over sodium sulfate and concentrated.

Yield: 144 g of a yellow oil, which is reacted as follows:

(b) 5-(4-Ethylphenyl)-3-hydroxy-2-cyclohexen-1-one 144 g (0.83 mol) of 4-(4-ethylphenyl)-3-buten-2-one dissolved in a small amount of methanol is dripped into 109 g (0.83 mol) of dimethyl malonate and 45 g (0.83 mol) of sodium methylate in 40 ml of methanol. The mixture is stirred at reflux for 3 hours and for 10 hours at room temperature. The methanol is distilled off, and the residue is taken up in 2 liters of 10% strength potassium hydroxide solution and stirred for 8 hours at room temperature. At 60° C., the mixture is acidified to pH 1 with concentrated hydrochloric acid. The mixture is stirred for a further 2 hours and suction filtered, and the precipitate is dried under reduced pressure.

Yield: 167 g of a yellow solid; m.p. 162°–164° C.

(c) 2- Butyryl-5-(4-ethylphenyl)-3-hydroxy-2-cyclohexen-1-one 51 g (0.51 mol) of triethylamine and—with ice cooling—54 g (0.51 mol) of butyryl chloride are dripped into a solution of 110 g 0.51mol) of the 5-(4-ethylphenyl)-3-hydroxy-2-cyclohexen-1-one, obtained in accordance with the foregoing instructions, in 500 ml of tetrahydrofuran. After 8 hours at room temperature, the mixture is filtered and the precipitate is washed with tetrahydrofuran. The filtrate is concentrated, the residue is taken up in 500 ml of ethyl acetate and 6.2 g of 4-N,N-dimethylaminopyridine is added. The homogeneous solution is kept for 40 hours at room temperature, is then concentrated and the residue is taken up in 10% strength potassium hydroxide solution. The undissolved constituents are separated off, and the filtrate is acidified to pH 1. The product which precipitates out is filtered off and dried under reduced pressure.

yield: 100 g of a yellow solid; m.p. 60°–62° C.

(d) 2-(E)-3-Chloro-2-propenyloxyiminobutyl-5-(4-ethylphenyl)-3-hydroxy-2- cyclohexen-1-one 16.6 g (0.12 mol) of (E)-3-chloro-2-propenyloxyamine hydrochloride and 9.7 g (0.12 mol) of sodium bicarbonate are added to 30 g (0.11 mol) of the 2-butyryl-5-(4-ethyiphenyl)-3-hydroxy-2-cyclohexen-1-one, obtained in accordance with the foregoing instructions, in 300 ml of methanol, and the solution is stirred overnight at room temperature. After concentration, the residue is taken up in 300 ml of dichloromethane and washed twice with water followed by drying over sodium sulfate and concentration.

Yield: 22 g of a yellow solid (active ingredient no. 11 in the table below); m.p. 56°–58° C.

The compounds of the formula I given in the table below are characterized by their melting point and/or $^1$H-NMR data. The $^1$H-NMR spectra were taken in deuterochloroform or hexadeuterosuifoxide as solvent, with tetramethylsilane as internal standard. The chemical shifts were registered in ppm. The multiplicities are given as follows: s=singlet, d=doublet, t=triplet, q=quartet, m=multiplet.

TABLE

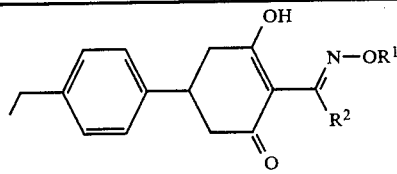

I

| Comp. No. | R$^2$ | R$^1$ | mp. (°C.) | $^1$H-NMR (δ in ppm) |
|---|---|---|---|---|
| 1 | ethyl | CH$_2$CH=CH$_2$ | | 1.15(t,3H), 1.22(t,3H), 2.64(q,2H), 4.54(d,2H) |
| 2 | ethyl | (E)-CH$_2$CH=CHCH$_3$ | 53–54 | 1.16(t,3H), 1.23(t,3H), 1.77(d,3H), 2.64(q,2H), 4.47(d,2H) |
| 3 | ethyl | (E)-CH$_2$CH=CHCl | | 1.16(t,3H), 1.23(t,3H), 2.64(q,2H), 4.52(d,2H) |
| 4 | ethyl | CH$_2$C≡CH | | 1.16(t,3H), 1.23(t,3H), 2.63(q,2H), 4.65(s,1H) |
| 5 | ethyl | CH$_2$C≡CCH$_3$ | | |
| 6 | ethyl | 5-Cl-2-thenyl | | 1.14(t,3H), 1.22(t,3H), 2.65(q,2H), 5.08(s,1H) |
| 7 | ethyl | CH$_2$CH$_2$Cl | | 1.17(t,3H), 1.23(t,3H), 2.61(q,2H), 3.70(t,2H), 4.31(t,2H) |
| 8 | ethyl | 3-methyl-5-isoxazolylmethyl | | 1.15(t,3H), 1.23(t,3H), 2.31(s,3H), 2.65(q,2H), 5.10(s,2H), 6.17(s,1H) |
| 9 | n-propyl | CH$_2$CH=CH$_2$ | | 0.98(t,3H), 1.24(t,3H), 2.63(q,2H) 4.54(d,2H) |
| 10 | n-propyl | (E)-CH$_2$CH=CHCH$_3$ | | 0.99(t,3H), 1.25(t,3H), 1.77(d,3H), 2.64(q,2H), 4.45(d,2H) |
| 11 | n-propyl | (E)-CH$_2$CH=CHCl | 56–58 | 0.97(t,3H), 1.24(t,3H), 2.63(q,2H), 4.52(d,2H) |
| 12 | n-propyl | CH$_2$C≡CH | | 0.98(t,3H), 1.26(t,3H), 4.68(s,1H) |
| 13 | n-propyl | CH$_2$C≡CCH$_3$ | | |
| 14 | n-propyl | 5-Cl-2-thenyl | | 0.96(t,3H), 1.23(t,3H), 2.64(q,2H), 5.10(s,2H) |
| 15 | n-propyl | CH$_2$CH$_2$Cl | | 0.98(t,3H), 1.23(t,3H), 2.64(q,2H), 3.72(t,2H), 4.32(t,2H) |
| 16 | n-propyl | 3-methyl-5-isoxazolylmethyl | 96–98 | 0.95(t,3H), 1.24(t,3H), 2.33(s,3H), 5.11(s,2H), 6.16(s,1H) |

USE EXAMPLES

The action of the cyclohexenone derivatives of the formula I on plant growth is demonstrated by the following greenhouse experiments:

The vessels employed were plastic flowerpots having a volume of 300 cm$^3$ and filled with a sandy loam containing about 3.0% humus. The seeds of the test plants were sown separately, according to species.

For the preemergence treatment, the active ingredients were applied to the surface of the soil immediately after the seeds had been sown. The compounds were emulsified or suspended in water as vehicle, and sprayed through finely distributing nozzles. The application rate was 0.5 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated. The application rate for postemergence treatment was 0.125 kg/ha. No covers were placed on the vessels in this method.

The pots were set up in the greenhouse, species from warmer climates in warmer areas (20° to 35° C.) and species from moderate climates at 10 to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were *Avena fatua, Alopecurus myosuroides, Digitaria sanguinalis, Echinochloa crus-galli, Lolium multiflorum. Medicago sativa, Triticum aestivum* and *Zea mays*.

Active ingredients 3 and 11, on preemergence application of 0.5 kg/ha, have a strong herbicidal action on grassy plants; mustard, as an example of a broadleaved species, remains undamaged.

For combating grassy vegetation, examples nos. 2 and 3 are suitable at a postemergence application rate of 0.125 kg/ha. Broadleaved crops, such as alfalfa, are not damaged. The novel active ingredients have a selective herbicidal action.

Active ingredients 3 and 11 may be used postemergence for combating unwanted grassy species in wheat. The crop plants only suffer minor damage, if any at all.

We claim:

1. A cyclohexenone compound of the formula I

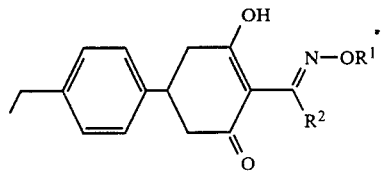

where the substituents have the following meanings:
$R^1$ is $C_3$-$C_4$-alkenyl, or $C_2$-$C_4$-haloalkenyl, and
$R^2$ is $C_1$-$C_4$-alkyl,
and their agriculturally acceptable salts.

2. A herbicidal composition which comprises a carrier or diluent and a herbicidally effective amount of a cyclohexenone derivative of the formula I as set forth in claim 1.

3. A process for combating the growth of unwanted plants, wherein the unwanted plants and/or their habitat are treated with a herbicidally effective amount of a cyclohexenone derivative of the formula I as set forth in claim 1.

4. A cyclohexenone compound of the formula I as set forth in claim 1, wherein $R^1$ is $CH_2CH=CH_2$ and $R^2$ is ethyl.

5. A cyclohexenone compound of the formula I as set forth in claim 1, wherein $R^1$ is (E)—$CH_2CH=CHCH_3$ and $R^2$ is ethyl.

6. A cyclohexenone compound of the formula I as set forth in claim 1, wherein $R^1$ is (E)—$CH_2$—$CH=CHCl$ and $R^2$ is ethyl.

7. A cyclohexenone compound of the formula I as set forth in claim 1, wherein $R^1$ is $CH_2CH=CH_2$ and $R^2$ is n-propyl.

8. A cyclohexenone compound of the formula I as set forth in claim 1, wherein $R^1$ is (E)—$CH_2$—$CH=CHCH_3$ and $R^2$ is n-propyl.

9. A cyclohexenone compound of the formula I as set forth in claim 1, wherein $R^1$ is (E)—$CH_2$—$CH=CHCl$ and $R^2$ is n-propyl.

* * * * *

UNITED STATES PATENT AND TRADEMARK OFFICE
CERTIFICATE OF CORRECTION

PATENT NO. : 4,994,106

DATED : Feb. 19, 1991

INVENTOR(S) : Dieter KOLASSA et al.

It is certified that error appears in the above-identified patent and that said Letters Patent is hereby corrected as shown below:

On the title page, item [75], "Karl-Otto Westphalen, Spever" should read —Karl-Otto Westphalen, Speyer—

Signed and Sealed this

Twelfth Day of October, 1993

Attest:

BRUCE LEHMAN

Attesting Officer

Commissioner of Patents and Trademarks